(12) United States Patent
Bellec et al.

(10) Patent No.: US 9,889,216 B2
(45) Date of Patent: Feb. 13, 2018

(54) ASSEMBLY CONSISTING OF A DECONTAMINATION DEVICE AND AT LEAST ONE PREFORM, FACILITY AND METHOD FOR PRODUCING A STERILE CONTAINER

(71) Applicant: SIDEL PARTICIPATIONS, Octeville sur Mer (FR)

(72) Inventors: Caroline Bellec, Octeville sur Mer (FR); Guy Feuilloley, Octeville sur Mer (FR)

(73) Assignee: SIDEL PARTICIPATIONS, Octeville sur Mer (FR)

( * ) Notice: Subject to any disclaimer, the term of this patent is extended or adjusted under 35 U.S.C. 154(b) by 669 days.

(21) Appl. No.: 14/360,015

(22) PCT Filed: Dec. 20, 2012

(86) PCT No.: PCT/EP2012/076413
§ 371 (c)(1),
(2) Date: May 22, 2014

(87) PCT Pub. No.: WO2013/092879
PCT Pub. Date: Jun. 27, 2013

(65) Prior Publication Data
US 2014/0265039 A1    Sep. 18, 2014

(30) Foreign Application Priority Data
Dec. 21, 2011  (FR) ..................... 11 62121

(51) Int. Cl.
*A61L 2/10*    (2006.01)
*A61L 2/08*    (2006.01)
(Continued)

(52) U.S. Cl.
CPC ................ *A61L 2/10* (2013.01); *A61L 2/085* (2013.01); *B29B 13/08* (2013.01);
(Continued)

(58) Field of Classification Search
CPC . B29B 13/08; A61L 2/10; A61L 2/085; A61L 2202/23; A61L 2202/11; A61L 2202/16
See application file for complete search history.

(56) References Cited

U.S. PATENT DOCUMENTS 3,712,784 A * 1/1973 Siard .................... A61L 2/04
                                                          134/166 R
4,592,719 A * 6/1986 Bellehache ......... B29C 45/4225
                                                                34/428
(Continued)

FOREIGN PATENT DOCUMENTS

EP          2 505 505    10/2012
KR       2005 0004663     1/2005
(Continued)

OTHER PUBLICATIONS

International Search Report dated Apr. 4, 2013, corresponding to PCT/EP2012/076413.
(Continued)

*Primary Examiner* — Yogendra N Gupta
*Assistant Examiner* — Emmanuel S Luk
(74) *Attorney, Agent, or Firm* — Young & Thompson

(57) ABSTRACT

The invention relates to an assembly (1) composed of at least one preform (12) and of a device (10) for decontaminating the interior of a preform (12) by irradiation with at least one type of ultraviolet radiation emitted by components (22) of the semiconductor type, relates to an installation (100) for producing a sterile recipient (120) including at least one
(Continued)

decontamination device (10) and relates to a method for fabricating a sterile recipient (120) starting from a decontaminated preform (12).

22 Claims, 4 Drawing Sheets

(51) Int. Cl.
    *B29B 13/08*     (2006.01)
    *B29K 667/00*     (2006.01)

(52) U.S. Cl.
    CPC ........ *A61L 2202/11* (2013.01); *A61L 2202/16* (2013.01); *A61L 2202/23* (2013.01); *B29K 2667/003* (2013.01)

(56) References Cited

U.S. PATENT DOCUMENTS

| | | | |
|---|---|---|---|
| 5,220,174 A * | 6/1993 | Oshida | B29C 71/04 250/492.1 |
| 2005/0053520 A1* | 3/2005 | Masaoka | A61L 2/186 422/62 |
| 2006/0113550 A1* | 6/2006 | Kim | H01L 33/32 257/79 |
| 2009/0274576 A1 | 11/2009 | Ressler | |
| 2009/0317506 A1* | 12/2009 | Adriansens | A61L 2/04 425/103 |
| 2010/0089906 A1* | 4/2010 | Plantamura | B29B 13/023 219/645 |
| 2011/0203579 A1* | 8/2011 | Quetel | B29B 13/025 126/85 R |
| 2012/0138969 A1* | 6/2012 | Moon | H01L 33/382 257/88 |
| 2012/0294760 A1 | 11/2012 | Humele et al. | |
| 2013/0133297 A1* | 5/2013 | Adriansens | B29C 49/46 53/558 |
| 2014/0140071 A1* | 5/2014 | Daicho | C09K 11/715 362/317 |

FOREIGN PATENT DOCUMENTS

| | | |
|---|---|---|
| KR | 100 686 703 | 2/2007 |
| WO | 99/03513 | 1/1999 |
| WO | 00/48819 | 8/2000 |
| WO | 02/36437 | 5/2002 |
| WO | 2004/031706 | 4/2004 |
| WO | 2006/136499 | 12/2006 |
| WO | 2007/051276 | 5/2007 |
| WO | 2008/024478 | 2/2008 |
| WO | 2008/049876 | 5/2008 |
| WO | 2010/071346 | 6/2010 |
| WO | 2012/141992 | 10/2012 |

OTHER PUBLICATIONS

French Search Report dated Aug. 10, 2012, corresponding to the Foreign Priority Application No. 1162121.

* cited by examiner

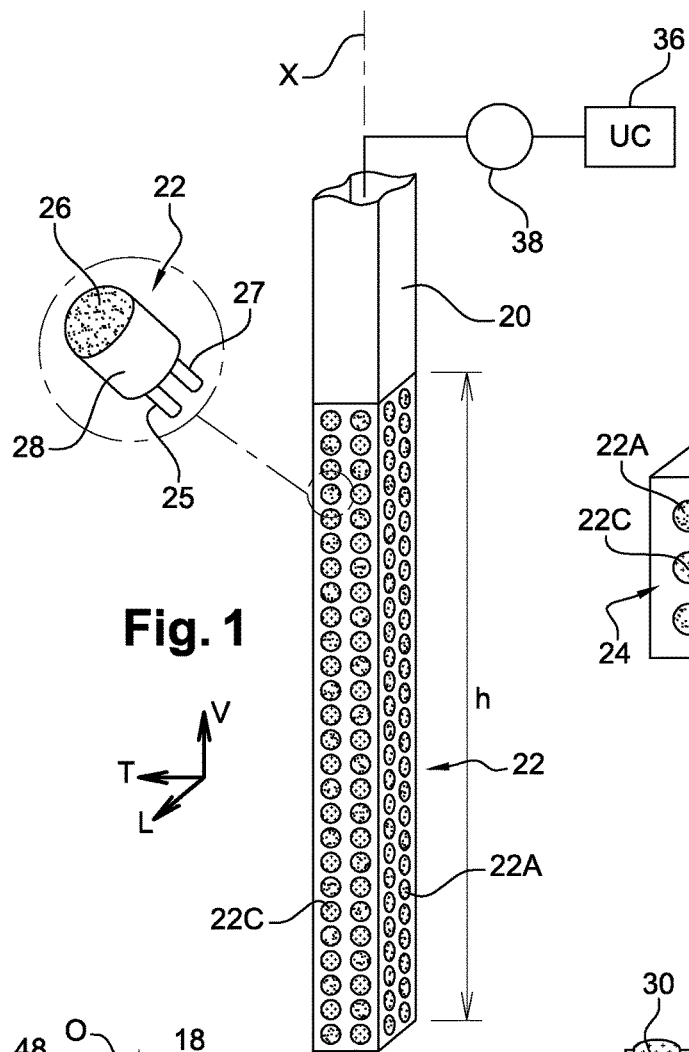
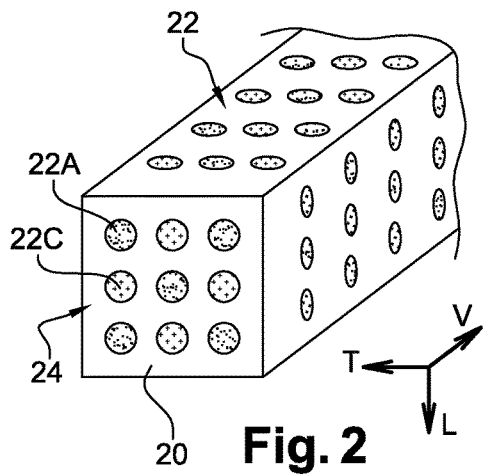
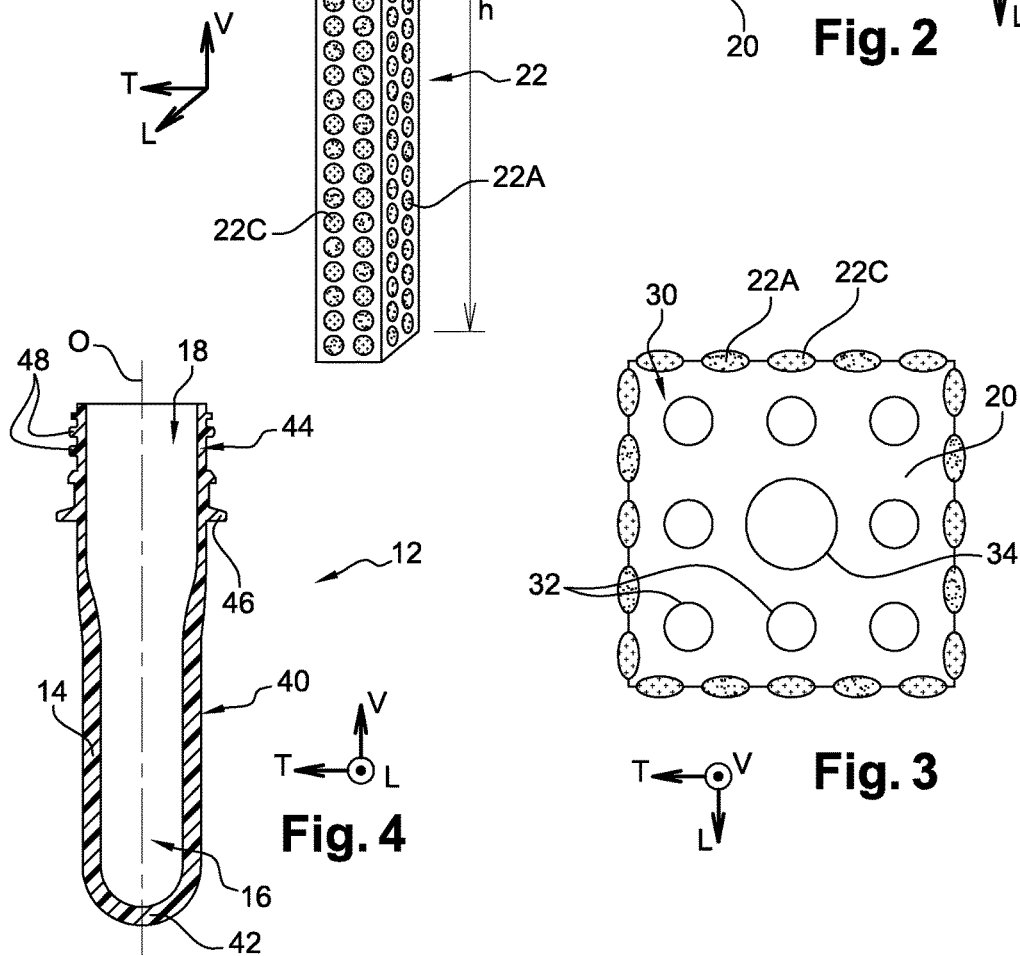
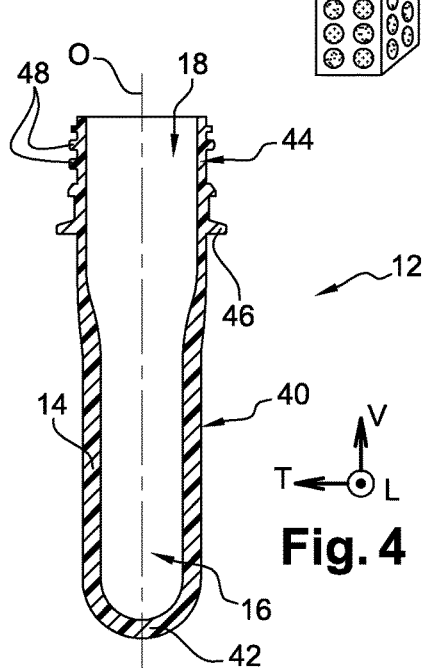
Fig. 1
Fig. 2
Fig. 3
Fig. 4

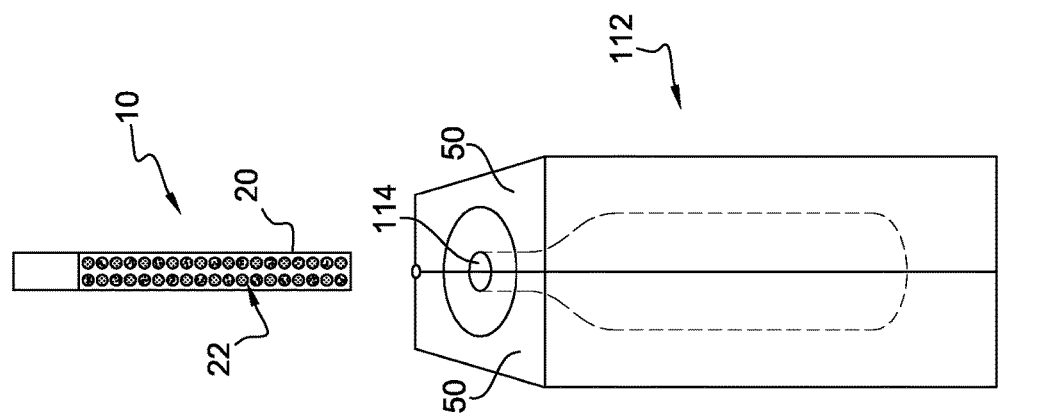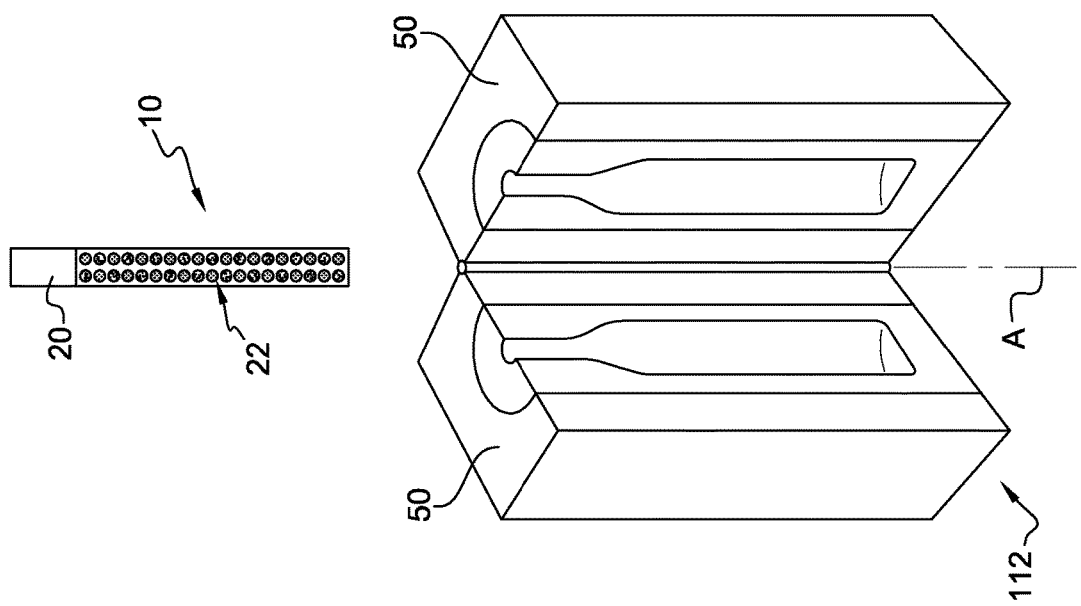
Fig. 7

ASSEMBLY CONSISTING OF A DECONTAMINATION DEVICE AND AT LEAST ONE PREFORM, FACILITY AND METHOD FOR PRODUCING A STERILE CONTAINER

BACKGROUND OF THE INVENTION

FIELD OF THE INVENTION

The invention relates to an assembly consisting of a decontamination device and at least one preform, an installation and a method for producing a sterile recipient.

The invention relates more particularly to an assembly comprising a device for decontamination the interior of preforms to and at least one preform made of thermoplastic material for the production of a recipient, in which the preform comprises a neck which is axially extended by a body closed by a bottom and which bounds an opening for access to the interior of said preform.

DESCRIPTION OF THE RELATED ART

In the field of agri-foodstuffs, decontamination devices are known for implementing a decontamination treatment (also known as aseptization or sterilization) of the interior of at least one preform made of thermoplastic material, such as PET.

Such devices are used for decontaminating, in particular, the interior of preforms which are designed to be transformed into recipients, the sterile recipients obtained being capable of receiving foodstuffs.

The aim of the decontamination treatments applied is to destroy, or at the very least to reduce, the presence of microbiological organisms or micro-organisms, such as in particular, germs, bacteria, spores, molds, etc.

In this regard, in decontamination devices, those are identified that implement a decontamination referred to as using "chemical processes" resulting from bactericide, virucide, fongicide, etc. actions of at least one sterilizing agent, such as notably hydrogen peroxide ($H_2O_2$).

The document WO-A1-2006/136499 describes one example of such a decontamination inside of a preform made of thermoplastic material by means of a deposition by condensation of a film of a sterilizing agent.

BRIEF SUMMARY OF THE INVENTION

The aim of the present invention is notably to provide an alternative to decontamination by chemical processes thanks to an assembly notably comprising a decontamination device allowing the interior of a preform to be decontaminated by irradiation.

For this purpose, the invention provides an assembly comprising a device for decontaminating the interior of preforms and at least one preform of the type previously described, characterized in that said decontamination device comprises at least one support mechanism carrying means for decontaminating by irradiation which consist of components of the semiconductor type designed to be introduced via the opening to the interior of said preform in order to selectively emit at least one type of ultraviolet radiation inside of the preform to be decontaminated.

Advantageously, the decontamination by irradiation is carried out prior to the transformation of the preform into a recipient.

Advantageously, the internal surface area of a preform to be decontaminated is smaller than that of the final recipient (bottle, flask, pot, etc.) such that the decontamination of a preform is more cost-effective, notably by virtue a lower consumption of energy.

In addition and by comparison with that of a recipient (such as a bottle) which is often engineered for technical and/or esthetic reasons, the internal surface of the wall of a preform does not comprise any elements with relief, so that no problem of shadowing or of surfaces being masked to the radiation is posed with a preform.

However, the introduction of the means for decontaminating by irradiation into the interior of a preform comes up against various technical problems of accessibility, which problems were not encountered using decontamination by chemical processes where, generally speaking, only the sterilizing agent projected from a nozzle is introduced via the opening of the neck.

A preform presents a reduced accessibility at the very least due to the single access to its closed internal volume via the opening bounded by the neck of the preform.

As approximate dimensions, the value of the internal diameter of the neck of a preform is generally in the range between 20 and 35 mm for preforms designed to be transformed into bottles, These values are not however limiting and are given solely by way of examples.

If the neck is a part of the preform which—by its internal diameter—determines the constraints on accessibility to the internal volume of the preform, it is not however always the only part to take into consideration.

Indeed, the body of the preform, which can comprise at least one axial section having an internal diameter less than or substantially equal to the internal diameter of the neck determining the opening, should also be considered.

It will be recalled that a preform is fabricated by injection of thermoplastic material into a mold, the point of injection being situated on the bottom of the preform.

Thus, the fact that the radial dimensions of at least one section of the body, for example that of the body directly adjacent to the neck or the bottom of the preform, are smaller than those of the neck is intended to facilitate the removal of the preform from the mold after fabrication.

As a non-limiting example and to give approximate dimensions, a preform with a total height of 80 mm and whose neck internal diameter is overall equal to a value of 22 mm will for example have an internal diameter on the section of the body adjacent to the bottom whose value will be in the range between 16 and 17 mm.

By virtue notably of their reduced dimensions, the semiconductor components forming the decontamination means are able to be introduced with their support mechanism into the interior of the preform through the opening of the neck and beyond into the closed internal volume which is bounded around the circumference by the internal surface of the wall of the neck, of the body and of the bottom of the preform.

Advantageously, the decontamination means according to the invention are indeed not only capable of being introduced via the small diameter opening of the neck of the preform, but also beyond into the body and close to the bottom without however coming into contact with the internal surface.

It is for these reasons that the decontamination means according to the invention are disposed in close proximity to the internal surface and irradiate the interior of the preform, and more precisely the whole of the internal surface of the wall of the preform, by means of said at least one type of ultraviolet radiation emitted by the semiconductor components.

By virtue of the fact that the source emitting radiation formed by the components of the semiconductor type is introduced directly into the interior of the preform, or received in the internal volume, the power emitted by each component is used in an optimum manner, with absolutely no loss, said at least one type of ultraviolet radiation traveling a short distance before irradiating the surface of the wall located globally facing it.

By comparison, it will notably be understood that an emitting source positioned on the outside of the preform would not allow an equivalent efficiency to be obtained between the energy consumed, on the one hand, and the quantity of radiation effectively received by the surface to be decontaminated by irradiation, on the other.

The irradiation by the one or more type(s) of radiation emitted by the decontamination means, for at least one given period of time, causes the destruction of all or of the major part of the aforementioned micro-organisms (germs, bacteria, spores, molds, etc.) present inside of the preform and allows, after transformation of said decontaminated preform, a sterile recipient to be obtained.

It is recalled that the quantity of micro-organisms is able to be quantified by counting notably after washing, filtering and culturing operations; a logarithmic reduction is thus determined in the number of micro-organisms, for example referred to as of the order of 3D, or alternatively 3 Log, equivalent to 1000 units ($10^3$).

Thanks to the device for decontaminating by irradiation designed according to the invention, the interior of the preform is sterilized with levels of decontamination which can reach values of the order of at least 3 Log and up to 6 Log.

The decontamination means are capable of selectively emitting at least one type of ultraviolet radiation exhibiting at least one main emission line having a wavelength in the range between 100 nm and 400 nm.

Preferably, the decontamination means are capable of emitting a combination of more than one type of radiation furthermore comprising at least one type of ultraviolet radiation of the "UVC" type and/or ultraviolet radiation of the "UVA" type, advantageously combined.

At least one of the types of ultraviolet radiation is combined with at least one other type of radiation of the infrared or "IR" type, preferably both types of ultraviolet radiation UVC and UVA.

Such an irradiating combination of at least two types of radiation allows a synergy effect to be obtained, thanks to which the irradiated micro-organisms are destroyed with higher rates of reduction of the number of micro-organisms.

Advantageously, the direct treatment applied with such an irradiating combination of types of radiation allows an effectiveness of destruction to be obtained over a large number of micro-organisms, each of the micro-organisms generally exhibiting a greater vulnerability to one of the radiations emitted in particular.

The applicant has been able to establish that the synergy effect of such an irradiating combination stems from the fact that, for example, the molds are more sensitive to infrared radiation, to whereas the bacteria will be more sensitive to ultraviolet radiation.

The decontaminating action of the infrared radiation results from the fact that a large quantity of heat is generated that is capable of altering the deoxyribonucleic acid (or DNA) but of above all causing an alteration of the membrane of the micro-organism, or even the implosion of the micro-organism that is incapable of dissipating it or of evacuating it.

The decontaminating action of the ultraviolet radiation results from different phenomena and especially from their capacity to pass through the membrane of the micro-organism in order to alter the deoxyribonucleic acid (or DNA) of its nucleus, for which reason both kinds of ultraviolet radiation UVC and UVA are particularly capable, by altering the DNA, of inhibiting the mitosis.

The device for decontaminating by irradiation advantageously allows levels of decontamination to be achieved which are at least equivalent to those obtained with a decontamination or sterilization by chemical processes for which it accordingly constitutes an alternative that can have industrial applications.

By means of the support mechanism passing through the opening of the neck of the preform, the emitting source carried by said mechanism is brought near to the wall bounding the internal closed volume, in front of the surface, in such a manner that an intense irradiation of the micro-organisms is obtained and accordingly the guarantee of their massive and rapid destruction.

Advantageously, the decontamination inside of the preform is obtained with a short irradiation time which consequently does not affect the production rate of recipients.

According to other features of the device of the invention:
at least one of the components forming said decontamination means emits ultraviolet radiation of the "C" type to exhibiting at least one main emission line having a wavelength in the range between 100 nm and 280 nm;
at least one of the components forming the decontamination means emits ultraviolet radiation of the "A" type exhibiting at least one main emission line having a wavelength in the range between 315 nm and 400 nm;
the decontamination means consist of the components forming at least a first group of component(s) and a second group of component(s), and at least the first group of component(s) consists of at least one component which emits ultraviolet radiation exhibiting at least one main emission line having a wavelength in the range between 100 nm and 400 nm;
the second group of component(s) consists of at least one component which emits infrared radiation exhibiting at least one main emission line having a wavelength in the range between 780 nm and 1 mm;
said decontamination device comprises actuation means selectively controlled for causing a relative movement between the support mechanism and the preform in order to temporarily introduce the means for decontamination by irradiation into the interior of the preform;
the decontamination means consist of the components which are arranged over all or part of the height of the section of the support mechanism designed to be received inside of the preform;
the decontamination means consist of the components which are arranged on the whole of the periphery of the support mechanism in order to emit radiation in all directions, over substantially 360°, in such a manner as to decontaminate the interior of the preform;
the support mechanism for the components is selectively driven in rotation so as to scan the interior of the preform with at least one type of ultraviolet radiation;

the decontamination device comprises a control unit selectively controlling the components in order to regulate the emission or otherwise of said at least one type of ultraviolet radiation;

the support mechanism for the components consists of a shaft for drawing from a preform molding unit for the fabrication of recipients;

the decontamination device comprises means for cooling the components, said means of cooling being composed at least of the support mechanism evacuating at least by conduction the heat produced in operation by said components;

the support mechanism comprises a cooling circuit for selectively establishing a circulation of a cooling fluid inside of the support mechanism;

at least a part of the components forming the decontamination means are light-emitting diodes;

at least a part of the components forming the decontamination means are laser diodes.

Advantageously, the decontamination device of the assembly according to the invention is used in an installation for production of sterile recipients which are obtained starting from preforms previously decontaminated by irradiation prior to their transformation.

The invention provides an installation for the production of sterile recipients starting from preforms made of thermoplastic material comprising a neck which is axially extended by a body closed by a bottom and which bounds an opening for access to the interior of said preform, said installation comprising at least:

an oven for heat treatment of the preforms;

a blowing machine for transforming, at least by injection of a fluid under pressure, said preforms into recipients;

characterized in that said installation comprises at least to one device for decontaminating the preforms comprising at least one support mechanism carrying means for decontamination by irradiation which consist of components of the semiconductor type designed to be introduced via the opening into the interior of said preform in order to selectively emit at least one type of ultraviolet radiation inside of the preform to be decontaminated.

The decontamination device is able to be arranged according to the direction of movement of the flow of preforms within the installation, upstream, in or downstream of the heat treatment oven Advantageously, said decontamination device is arranged upstream of the heat treatment oven.

As a variant, said decontamination device is integrated into the heat treatment oven, notably into the device for transporting the preforms between the entry and the exit of the oven.

Advantageously, said decontamination device is arranged downstream of the heat treatment oven, notably integrated into the means for transferring the preforms coming from the oven or integrated into the blowing machine.

The invention furthermore provides a method for fabricating a sterile recipient starting from a preform made of thermoplastic material, said method comprising at least:

an initial step consisting in fabricating a preform made of thermoplastic material, a final step consisting in transforming said preform into a recipient, characterized in that, between said initial and final steps, said method comprises at least one intermediate step for decontamination of at least the interior of a preform consisting at least in:

introducing into the interior of the preform means for decontamination by irradiation formed by components of the semiconductor type capable of selectively emitting at least one type of ultraviolet radiation;

controlling said components of the semiconductor type so as to cause the emission of at least one type of ultraviolet radiation in order to irradiate the interior of the preform;

extracting said decontamination means outside of the decontaminated preform.

Advantageously, the method comprises a step for heat treatment of the preform prior to the final step for transformation of the preform into a recipient.

Advantageously, the final step consists at least in injecting a fluid under pressure into the interior of a preform previously heat treated and disposed in a unit for molding a recipient.

The decontaminated preform is thus transformed into a sterile recipient within a molding unit, notably by blowing or by drawing-blowing.

BRIEF DESCRIPTION OF THE DRAWINGS

Other features and advantages of the invention will become apparent upon reading the detailed description that follows for the understanding of which reference will be made to the appended drawings in which:

FIG. 1 is a perspective view which shows one embodiment of a decontamination device for an assembly according to the invention and which illustrates a support mechanism on which components of the semiconductor type are mounted forming the means for decontamination by irradiation of said device;

FIG. 2 is a perspective view which shows the free end of the support mechanism for the decontamination device according to FIG. 1;

FIG. 3 is a cross-sectional view of the support mechanism for the decontamination device according to FIG. 1 which shows means for cooling the decontamination means;

FIG. 4 is a cross-sectional view of one example of a to preform to be decontaminated before its transformation into a recipient by means of a decontamination device;

FIG. 7 is a perspective view which shows a molding unit comprising a drawing shaft forming the support mechanism for the decontamination means and which illustrates said unit in the open position and in the closed position.

DETAILED DESCRIPTION OF THE PREFERRED EMBODIMENTS

In the description and the claims, the terms such as "upper" and "lower", "internal" and "external", etc. will be used in a non-limiting manner with reference to the definitions given in the description and to the reference frame (L, V, T) shown in the figures.

In addition, identical, similar or analogous elements will be designated by the same reference numbers.

FIGS. 1 to 3 show a decontamination device 10 according to one embodiment given as a non-limiting example.

According to the invention, the device 10 is used for carrying out the decontamination on the inside of at least one preform 12 such as is shown in FIG. 4.

Figure 5:
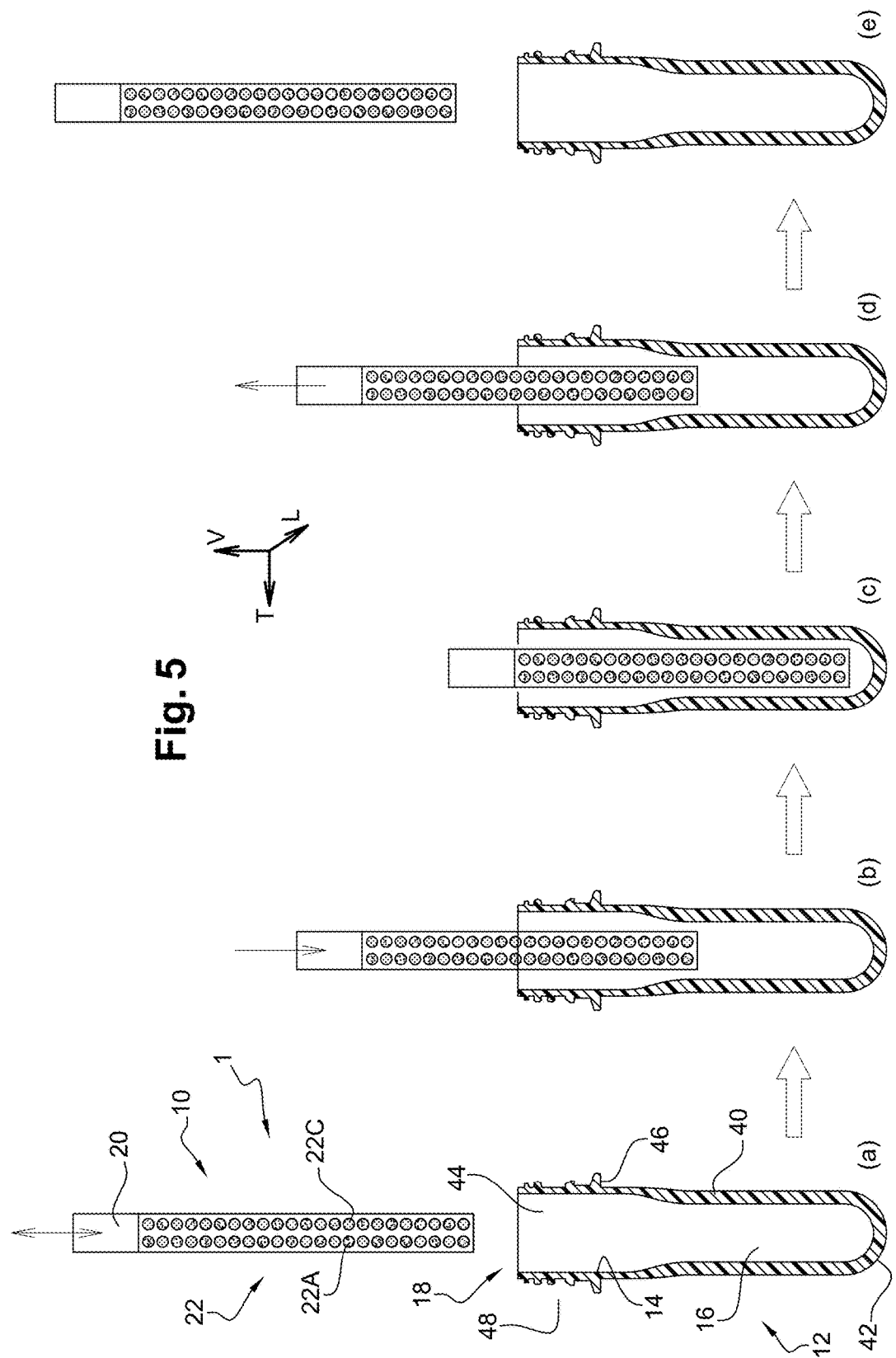
FIG. 5 is a schematic view which shows the successive steps for decontaminating the inside of a preform by the device for decontamination by irradiation in FIGS. 1 to 3.

An assembly 1 according to the invention shown in FIG. 5 comprises at least one preform 12 to be decontaminated by means of said associated decontamination device 10.

The preform 12 is notably characterized by a wall 14 bounding an internal closed volume 16 only accessible through an opening 18 circumferentially bounded by a neck.

One exemplary embodiment of a preform 12 will be described in more detail later on with reference to FIG. 4.

First of all, the decontamination device 10 will be described to according to one embodiment illustrated in FIGS. 1 to 3.

The decontamination device 10 comprises at least one support mechanism 20 which is capable of being selectively introduced via the opening 18 into the interior of the preform 12.

More precisely, at least a part of the support mechanism 20 forming its free end is designed to be received within the internal volume 16 of the preform 12.

The decontamination device 10 comprises means 22 for decontamination by irradiation which consist of components of the semiconductor type.

The components of the semiconductor type are capable of selectively emitting at least one type of ultraviolet radiation capable of destroying micro-organisms, or at the very least of inhibiting their development by preventing the mitosis, in order to sterilize the interior of the preform 12 and especially the surface of the internal wall 14.

The decontamination device 10 comprises at least one support mechanism 20 which carries means 22 for decontamination by irradiation which consist of components of the semiconductor type designed to be introduced via the opening 18 into the interior of the preform 12 in order to selectively emit at least one type of ultraviolet radiation inside of the preform 12 in such a manner as to sterilize the interior of the preform 12.

The support mechanism 20 for the decontamination device 10 globally takes the form of a shaft which extends in a rectilinear manner in the vertical direction of the reference frame (L, V, T) shown in FIG. 1.

In the present description, the vertical direction is used by convention, without reference to the Earth's gravity.

Preferably, the support mechanism 20 has, in cross-section across a horizontal plane (L, T), a polygonal shape capable of facilitating the mounting of the components, notably due to the planarity of the faces.

In the embodiment in FIGS. 1 to 3, the support mechanism 20 has a square cross-section. As a variant, the support mechanism 20 has a cross-section in the shape of a pentagon, hexagon, etc. or alternatively is triangular.

Advantageously, the components are disposed around the whole of the periphery of the support mechanism 20, preferably in a regular manner on the vertical faces of the mechanism 20.

The components are arranged vertically from the free end of the support mechanism 20 at least over a given height "h" corresponding for example to the section of the mechanism 20 designed to penetrate into the interior of the preform 12.

Preferably, the support mechanism 20 comprises components on its lower face 24, here horizontal, situated at its free end as is more particularly illustrated in FIG. 2.

As a variant, the support mechanism 20 does not comprise any components at its free end, in particular according to the geometry of this end as a pointed shape resulting in the absence of any horizontal lower face.

Advantageously, the components forming said decontamination means 22 are disposed on the support mechanism 20 in such a manner as to emit a radiation in all directions, over substantially 360°, in order to sterilize the whole of the inside of the preform 12.

Advantageously, the reflections of the emitted radiation or radiations which take place inside of the preform also participate in improving the sterilization inside of said preform 12.

The support mechanism 20 for the components has a main axis X which runs in the vertical direction of the reference frame (L, V, T) in FIG. 1.

Preferably, the support mechanism 20 is at least assembled so as to be mobile in translation in the vertical direction, sliding between at least a first position and a second to position.

As a variant, the support mechanism 20 is fixed vertically along the axis X and the preform 12 is then advantageously able to be selectively moved so as to introduce, via the opening 18, at least the part of the support mechanism 20 carrying the components into the preform 12.

Advantageously, the support mechanism 20 and the preform 12 are able to be selectively moved relative to one another, at least one of the two being mobile with respect to the other.

As a variant, the support mechanism 20 is capable of being selectively driven in rotation about the axis X, in such a manner as to allow scanning inside of the preform 12 by said at least one type of ultraviolet radiation emitted by the irradiating source forming the decontamination means 22.

Advantageously, said components forming the means 22 for decontamination by irradiation comprise a source of ultraviolet radiation exhibiting at least one main emission line having a wavelength in the range between 100 nm and 400 nm.

The various types of radiation within the spectral band of wavelength in the range between 100 nm and 400 nm, corresponding to said ultraviolet radiation, are conventionally differentiated by letters.

Thus, ultraviolet radiation of the "C" type, known as UVC, corresponds to a wavelength in the range between 100 nm and 280 nm, ultraviolet radiation of the "B" type, known as UVB, to a wavelength in the range between 280 nm and 315 nm and ultraviolet radiation of the "A" type, known as UVA, to a wavelength in the range between 315 nm and 400 nm.

Advantageously, at least one component forming the decontamination means 22 is capable of emitting ultraviolet radiation of the "C" type, in other words radiation exhibiting at least one main emission line having a wavelength in the range between 100 nm and 280 nm.

Preferably, said main emission line of the ultraviolet radiation of the "C" type has a wavelength in the range between 250 nm and 275 nm.

Advantageously, the section of wavelength in the range between 250 nm and 275 nm corresponds to the values for which the absorption of the radiation by the deoxyribonucleic acid (or DNA) of the micro-organisms is the highest and consequently where the destruction of the micro-organisms is maximum.

Indeed, deoxyribonucleic acid comprises four nitrogen-containing bases, namely adenine (A), thymine (T), cytosine (C) and guanine (G), which respectively exhibit characteristics for absorption of a different ultraviolet radiation.

Preferably, said main emission line of the ultraviolet radiation of the "C" type has a wavelength which is equal to 265 nm.

The value of 265 nm corresponds to the absorption peak of ultraviolet radiation by the deoxyribonucleic acid of micro-organisms such as for example the bacillus "*Bacillus Subtilis*".

Advantageously, the components forming the decontamination means 22 are capable of emitting various types of radiation, including within the spectral band corresponding to the ultraviolet.

Preferably, at least one component forming the decontamination means 22 is capable of emitting ultraviolet radiation of the "A" type, or UVA, exhibiting at least one main emission line having a wavelength in the range between 315 nm and 400 nm.

The decontamination means 22 may therefore consist of components that differ from one another at least by the characteristics of the emitted radiation.

Preferably, the decontamination means 22 then comprise at least a first group of component(s) and a second group of component(s).

Advantageously, at least the first group of component(s) consists of at least one component capable of emitting an ultraviolet radiation exhibiting at least one main emission line having a wavelength in the range between 100 nm and 400 nm.

Thus, the decontamination means 22 may comprise only components emitting ultraviolet radiation (UVC) or components emitting ultraviolet radiation (UVA) so as to form said first group of components.

Advantageously, the decontamination means 22 comprise components of each type either a first group of components capable of emitting ultraviolet radiation of the "C" type and a second group of components capable of emitting ultraviolet radiation of the "A" type.

The second group of component(s) is therefore then composed of at least one component capable of emitting ultraviolet radiation of the "A" type exhibiting at least one main emission line having a wavelength in the range between 315 nm and 400 nm, in other words also in the range between 100 nm and 400 nm.

As a variant, the second group of component(s) consists of at least one component capable of emitting radiation exhibiting at least one main emission line having a wavelength outside of the spectral band corresponding to the ultraviolet which is in the range between 100 nm and 400 nm.

Preferably, the second group of component(s) consists of at least one component capable of emitting an infrared radiation exhibiting at least one main emission line having a wavelength in the range between 780 nm and 1 mm.

As a variant, the decontamination means 22 of the device 10 consequently comprise at least three groups of different components, respectively capable of emitting ultraviolet radiation of the "C" and "A" type for the first and the second group together with infrared radiation for the third group.

As a consequence, the decontamination means 22 are advantageously able to combine at least two radiations of a given type, at least one of which belongs to the ultraviolet, for sterilizing by irradiation the interior of the preform.

Thanks to an irradiating combination resulting from the presence of at least two separate groups of components on the support mechanism 20, surprisingly, a synergy effect is obtained between said at least two types of radiation emitted simultaneously for treating the interior of the preform 12, which synergy effect enhances the destruction of the micro-organisms.

The number of components of a given type forming the first group is for example different from that of the second group of components such that, depending on the number of respective components of each type, the types of radiation emitted can be made to vary in proportion.

The power of the radiation emitted by a given group of components is also able to differ from that of another group of components.

Preferably, at least a part of the components forming said decontamination means 22 are light-emitting diodes.

Advantageously, the light-emitting diodes exhibit a narrow emission spectral band around the chosen main emission line.

Such light-emitting diodes are for example, according to their acronyms, LEDs (Light Emitting Diode) or VCSELs (Vertical Cavity Surface Emitting Light) or else EEDs (Edge Emitting Diode).

In the decontamination device 10 according to the embodiment shown in FIGS. 1 to 3, the decontamination means 22 are light-emitting diodes, preferably said diodes are of the LED type.

FIG. 1 shows, in detail in a magnification circle, one example of a light-emitting diode mainly comprising an upper part 26 designed to be traversed by the radiation emitted from a lower part accommodated in a housing 28 from which run an anode 25 and a cathode 27 for the electrical power supply of the diode.

It goes without saying that the light-emitting diode shown in FIG. 1 is only one non-limiting example of a light-emitting diode.

The upper part 26 of the diode is advantageously a part exhibiting optical properties for scattering and/or reflecting the radiation emitted by the adjacent semiconductor means forming the lower part accommodated in the housing 28.

In a known manner, said semiconductor means correspond to the various layers of semiconductor material capable of emitting the radiation, said layers being generally supported by a 'base' which is more commonly referred to as a "submount".

As a variant not shown, the light-emitting or laser diode forming the semiconductor component may notably not comprise a housing 28.

According to such a variant, the diode is directly mounted onto the support mechanism 20 by means of the submount. Advantageously, the support mechanism 20 is then an element participant in the dissipation of the heat produced by the component in operation.

The element associated with the submount that provides the function of heat exchanger capable of dissipating heat is generally called "heat sink".

The absence of housing 28 according to such a variant advantageously allows the installation, for the same surface area, of a larger number of components.

Advantageously and especially with such a variant, a reduction of the overall size of the decontamination device is obtained by integrating the components into the support to mechanism 20, in such a manner that said components do notably not protrude and are protected from the environment (humidity, dust, etc.).

Preferably, the components are totally integrated into the thickness of the support mechanism 20 so as not to protrude with respect to the faces of said mechanism, by virtue of which the compactness of the decontamination device is increased.

The light-emitting diodes can be individual components but are preferably sub-assemblies, for example in the form of a bar or of a plate, each sub-assembly comprising a plurality of diodes.

Preferably, the decontamination means 22 comprise a first group of light-emitting diodes capable of emitting ultraviolet radiation of the UVC type and a second group of light-emitting diodes capable of emitting ultraviolet radiation of the UVA type.

In FIG. 1, the diodes referenced 22C correspond to the first group emitting radiation of the UVC type and the diodes referenced 22A correspond to the second group emitting radiation of the UVA type, each of the light-emitting diodes 22C and 22A of the LED type having been shown with different patterns in the part 26 in such a manner as to distinguish between them.

According to one variant not shown, the decontamination means 22 comprise light-emitting diodes emitting infrared radiation in combination with other diodes emitting ultraviolet radiation of the UVC type and/or of the UVA type.

As a variant, at least a part of the components forming the decontamination means 22 of the decontamination device 10 consist of laser diodes.

Laser diodes indeed exhibit an emission of the monochromatic or pseudo-monochromatic type allowing a radiation having a main emission line of a given wavelength to be obtained.

Advantageously, the decontamination device 10 comprises cooling means 30 capable of cooling the semiconductor components forming the decontamination means 22.

Indeed, in operation, components of the semiconductor type such as diodes produce heat; the components are therefore advantageously cooled notably in such a manner as to guarantee their optimum operation.

The cooling means 30 are for example formed by the support mechanism 20 which is capable of evacuating, by conduction, the heat produced in operation by the components mounted on the mechanism 20.

In order to promote the conduction of the heat by the support mechanism 20, the choice of the material composing said support mechanism 20 will be oriented toward a metal material exhibiting good thermal conductivity properties.

The support mechanism 20 can be equipped with means for dissipating the heat transmitted by conduction by the components, for example a radiator arranged on a section of the support mechanism 20 which is not introduced into the interior of the preform 12, where said radiator can be associated with a fan in order to force the heat exchange between the radiator and the air.

Preferably, the cooling means 30 are means allowing a regulation of the temperature in order to maintain the components under optimum operating conditions.

Advantageously, the support mechanism 20 incorporates a cooling circuit capable of selectively establishing a circulation of a cooling fluid inside of the support mechanism 20 for the components.

The cooling circuit comprises at least two conduits, respectively at least one admission conduit 32 and at least one evacuation conduit 34.

The conduits 32, 34 are respectively arranged within the support mechanism 20, a liquid preferably forming the fluid for cooling the components which is designed to be flowed through said conduits 32, 34 of the cooling circuit.

Such as illustrated in FIG. 3, the cooling circuit comprises a conduit 34 for evacuating the fluid which is arranged in a central position and connected to several conduits 32 for admission of the cooling fluid. The admission conduits 32 surround said evacuation conduit 34 and are adjacent to the faces of the support mechanism 20 on which the components are mounted.

Advantageously, all of the conduits 32 and 34 are directly formed in the material composing the support mechanism 20 ensuring the transmission by conduction of the heat produced by the components, from the faces of the support mechanism 20 as far as the admission conduits 34 thus providing the cooling, the heat absorbed being subsequently evacuated by the cooling fluid via the evacuation conduit 34.

According to one variant embodiment not shown, the cooling fluid of the cooling circuit consists of air circulating in at least one internal channel of the support mechanism 20.

Advantageously, the decontamination device 10 comprises a control unit 36 capable of selectively controlling each of the components or group of components in order to regulate the emission or otherwise of said at least one type of ultraviolet radiation.

Advantageously, the control unit 36 of the decontamination device 10 is capable of selectively controlling actuation means 38 so as to cause a relative movement between the support mechanism 20 and the preform 12 in order to execute a decontamination cycle.

Preferably and such as previously described, the support mechanism 20 is capable of sliding in the vertical direction, the actuation means 38 therefore being associated with the support mechanism 20.

The actuation means 38 consist for example of at least one actuator, such as an electric motor or a pneumatic or hydraulic cylinder drive.

The decontamination cycle comprises successively at least a phase for introduction, via said opening 18, of the decontamination means 22 into the closed internal volume 16 in order to sterilize the interior of the preform 12 and a phase for extraction, via the opening 18, of the decontamination means 22 outside of said closed internal volume 16 of the preform 12.

One example of a preform 12 will now be described in detail with reference to FIG. 4 then, with reference to FIG. 5, an assembly 1 according to the invention comprising such a preform 12 and a decontamination device 10 according to the embodiment which has just been described.

The preform 12 shown in FIG. 4 only constitutes one example of a preform made from thermoplastic material which is consequently presented by way of non-limiting example, the geometrical characteristics of a preform being in particular dependent on the desired final recipient, such as a bottle, a flask, a pot, etc., and on its intended contents.

The preform 12 comprises a body 40 whose wall 14 bounds the closed internal volume 16, a part of the wall 14 forming a bottom 42 opposite which, in the vertical direction of the reference frame (L, V, T), a neck 44 bounds said opening 18 for access to the internal volume 16.

The preform 12 has a main axis O which runs in the vertical direction.

In a known manner, the neck 44 of the preform is at its definitive shape and is attached to the body 40, here by a flange 46 aligned radially toward the outside.

The neck 44 of the preform is preferably equipped with a threaded surface 48 designed to allow the later closing off by capping of the final recipient.

The final sterile recipient is obtained after transformation of the decontaminated preform 12.

It will be recalled that the transformation of the preform 12 is obtained by means of at least one fluid under pressure introduced via the opening 18 into the interior of the preform 12 disposed in a molding unit comprising a mold corresponding to the recipient. Generally speaking, the fluid is air under pressure and the recipient obtained by blowing or by drawing-blowing of the preform.

For this purpose, the preform made of thermoplastic material is previously heat treated in an oven in order to soften the material composing it, which corresponds to the assumption under which the preform is not immediately transformed after its fabrication by injection.

The recipients such as bottles are used in the agri-foodstuffs industry for the conditioning of many liquids such as water, fruit juice or sodas, milk, etc.

In order to carry out an aseptic or sterile conditioning of such liquid products, decontamination devices are used for decontaminating at least the interior of the preform 12.

The aforementioned document WO-2006/136499 describes a method of sterilization for the decontamination of a preform made of thermoplastic material designed to be transformed into a sterile recipient.

In this document, at least the interior of the preform is chemically decontaminated by depositing a mist film of a sterilizing agent, such as hydrogen peroxide ($H_2O_2$), by condensation on the internal surface of the preform.

For many applications, such a method is satisfactory, in particular with regard to the degree of aseptization or of sterilization obtained after decontamination of the treated preforms.

As has been indicated in the introduction, other alternative methods to chemical decontamination are however sought in order notably to overcome certain constraints linked to the use of agents such as hydrogen peroxide ($H_2O_2$), often used for performing such a microbiological decontamination.

In the case of a preform made of thermoplastic material such as that shown in FIG. 4 and such as recalled in the introduction, the geometrical characteristics are directly linked to the desired type of recipient and often constitute an obstacle to the implementation of the decontamination, from the reduced dimensions of the opening 18 bounded by the neck 44 to the length and the narrowness of the body 40 extending from said neck 44 down to the bottom 42.

The internal diameter of the neck 44 of the preform 12 determines the opening 18 and, even though the values vary according to the recipient, it will be understood that the decontamination device 10 must advantageously be as small as possible.

Nevertheless, the neck 44 is not necessarily the part of the preform 12 having the smallest dimensions.

Indeed, the preform 12 illustrated in FIG. 4 has for example a body 40 connecting to the neck 44 via a truncated conical section, the internal diameter of the body 40 being smaller than the internal diameter of the neck 44.

The internal space in the neighborhood of the bottom 42 is also sometimes smaller than in the neck 44 owing to a greater thickness of the wall forming the bottom 42.

The thermoplastic material forming the preform, such as for example Polyethylene Terephthalate (PET), is also a characteristic to be taken into consideration during the choice of the method in order that the treatment does not cause any defects to the aspect, notably esthetic, of the recipient or else the presence of residues of the agent used for the sterilization.

However, thermoplastic materials such as PET form a barrier to ultraviolet radiation which cannot therefore pass through the wall 14 of the preform 12.

As a consequence, the decontamination treatment by irradiation inside of a preform 12 cannot be carried out from the outside of the preform 12 through the wall 14.

However, irradiation by ultraviolet radiation from the outside of the preform 12 may be implemented for decontaminating especially the outside of the neck 44 which constitutes a sensitive area.

Thus, the use of at least one type of ultraviolet radiation for sterilizing by irradiation the interior of the preform 12 requires the ultraviolet radiation to be introduced into the interior of the preform 12.

With the decontamination device 10 according to FIGS. 1 to 3, the emitting source itself, composed of semiconductor components, is advantageously introduced directly into the interior of the preform 12.

The treatment of such a preform 12 following a decontamination cycle carried out by means of said device 10 for decontamination by irradiation will now more particularly be described with reference to FIG. 5.

First of all, the preform 12 and/or the support mechanism 20 are moved so as to be positioned relative to one another in a given treatment position, the main axis X of the support mechanism 20 and the axis O of the preform being substantially coaxial.

As illustrated at (a) in FIG. 5, the support mechanism 20 is in the treatment position directly above the preform 12.

The support mechanism 20 then occupies a first position in which the mechanism 20 is on the outside of the preform 12 and which corresponds to a position waiting for the start of the decontamination cycle.

Preferably, the decontamination means 22 are inactive in the standby state.

According to the embodiment in FIGS. 1 to 3, the diodes 22C and 22A are therefore respectively switched off such that no ultraviolet radiation is emitted by the diodes.

Then, the control unit 36 of the decontamination device 10 then sends a command to the actuation means 38 associated with the support mechanism 20 to move the support mechanism 20 vertically from the first position to at least a second position.

The second position corresponds to an active position in which at least a part of the support mechanism 20 extends into the interior of the preform 12 to be decontaminated.

The phase for introduction of the source of radiation is illustrated at (b) in FIG. 5, the actuation means 38 here causing the support mechanism 20 to descend in the direction of the opening 18 of the neck 44 of the preform 12, here positioned "neck upward".

It goes without saying that the configuration of the preform 12 and of the support mechanism 20 could be structurally reversed.

As a variant, the preform 12 being positioned neck downward, the support mechanism 20 then performs a lifting movement in the direction of the opening 18 of the preform 12 so as to be introduced into the interior of the internal volume 16 of the preform 12 closed by the bottom 42.

Preferably, the support mechanism 20 is assembled so as to be mobile along the axis X with respect to the preform 12.

The support mechanism 20 is moved by the associated actuation means 38 which are selectively controlled for introducing it into the interior of the preform 12 then for extracting it from the preform.

As a variant, the support mechanism 20 is fixed and the preform 12 is able to be moved for example by gripping means assembled so as to be mobile.

The free end of the support mechanism 20 penetrates progressively into the interior of the preform 12 through the opening 18 circumferentially bounded by the neck 44.

Advantageously, the control unit 36 controls the decontamination means 22 and the diodes 22C and 22A are progressively turned on, at the same time as the free end of the support mechanism 20 for the diodes is introduced inside of the preform 12, into the closed internal volume 16 bounded by the wall 14.

The diodes 22C and 22A will therefore respectively emit their ultraviolet radiation as soon as they have passed through the opening 18 of the neck 44 of the preform 12 in such a manner that, in parallel with the movement of the support mechanism 20, the components will irradiate with the emitted one or more type(s) of radiation the surface of the wall 14 situated in front of them.

Thus, all the way down the descent of the support mechanism 20 until it reaches the second position of the mechanism 20 illustrated at (c) in FIG. 5, the internal wall 14 is irradiated from top to bottom.

Advantageously, the fact that the irradiation is started as soon as the mechanism passes through the opening 18, and without waiting for it to reach the second position, allows the duration of irradiation to be increased during the decontamination cycle.

Once the support mechanism 20 has arrived at the second position, it advantageously comes to a stop before travelling back in the reverse direction, in other words before being raised back up to the first position.

The time delay applied by the support mechanism 20 is designed to irradiate the bottom 42 of the preform 12 for a given sufficient period of time which depends on the applications.

As illustrated in FIG. 5, the diodes are shown inside of the preform 12 with no pattern on the part 26 so as to distinguish between them in order to illustrate by comparison the fact that the diodes are lit, the emitted one or type(s) of radiation not, for their part, having been shown.

Thus, at (c), all of the diodes 22C and 22A being lit irradiate the interior of the preform 12 with an ultraviolet radiation advantageously combining UVC and UVA radiation.

Advantageously, the height "h" over which diodes are installed on the support mechanism 20 corresponds substantially to at least the depth of the preform 12.

Advantageously and thanks to the lighting of the components selectively controlled by the control unit 36, the same support mechanism 20 can be used for treating preforms 12 with different dimensions, especially those of the body 40, the height "h" being variable by selectively controlling the lighting of one part only of the components.

As illustrated at (d) in FIG. 5, the control unit 36 of the decontamination device 10 subsequently sends a command to the actuation means 38 associated with the support mechanism 20 to move the support mechanism 20 vertically from its second position toward its first position, which corresponds to the extraction phase.

The support mechanism 20 is raised back up vertically along the axis X and the diodes 22C and 22A are controlled by the unit 36 in such a manner as to be extinguished when they again pass through the opening 18 of the neck 44 and return to the outside of the preform 12.

As illustrated at (e) in FIG. 5, the raising of the support mechanism 20 has ended and it again occupies its first position, all of the diodes 22C and 22A are extinguished, and a new decontamination cycle of another preform 12 can then advantageously begin.

The decontamination inside of a preform 12 comprises at least the steps consisting in:

introducing the means 22 for decontamination by irradiation formed by the semiconductor components into the interior of the preform 12;

controlling the semiconductor components so as to cause the emission of at least one type of ultraviolet radiation in order to decontaminate the interior of the preform 12 by irradiation;

extracting the decontamination means 22 outside of the preform 12.

Preferably and such as describes with reference to FIG. 5, the first step for introduction of the irradiating source into the preform 12 is obtained by sending a command to the actuation means 38 associated with the support mechanism 20 for the semiconductor components to move said support mechanism 20, from a first standby position toward a second working position, in such a manner as to introduce the emitting source inside of the closed internal volume 16 of the preform 12.

During the second step for irradiation for the purposes of decontamination, the components such as the diodes 22C and 22A forming the decontamination means 22 are selectively lit, at the latest when the support mechanism 20 has reached said second position.

The third step consists in sending a command to the actuation means 38 associated with the support mechanism 20 for the semiconductor components to move said support mechanism 20 in the opposite direction, this being from the second working position toward the first standby position initially occupied.

Advantageously, the decontamination device 10 which has just been described constitutes an autonomous treatment device that can be incorporated into an installation 100 for the production of recipients, such as bottles, in order to fabricate sterile recipients starting from decontaminated preforms.

Figure 6:
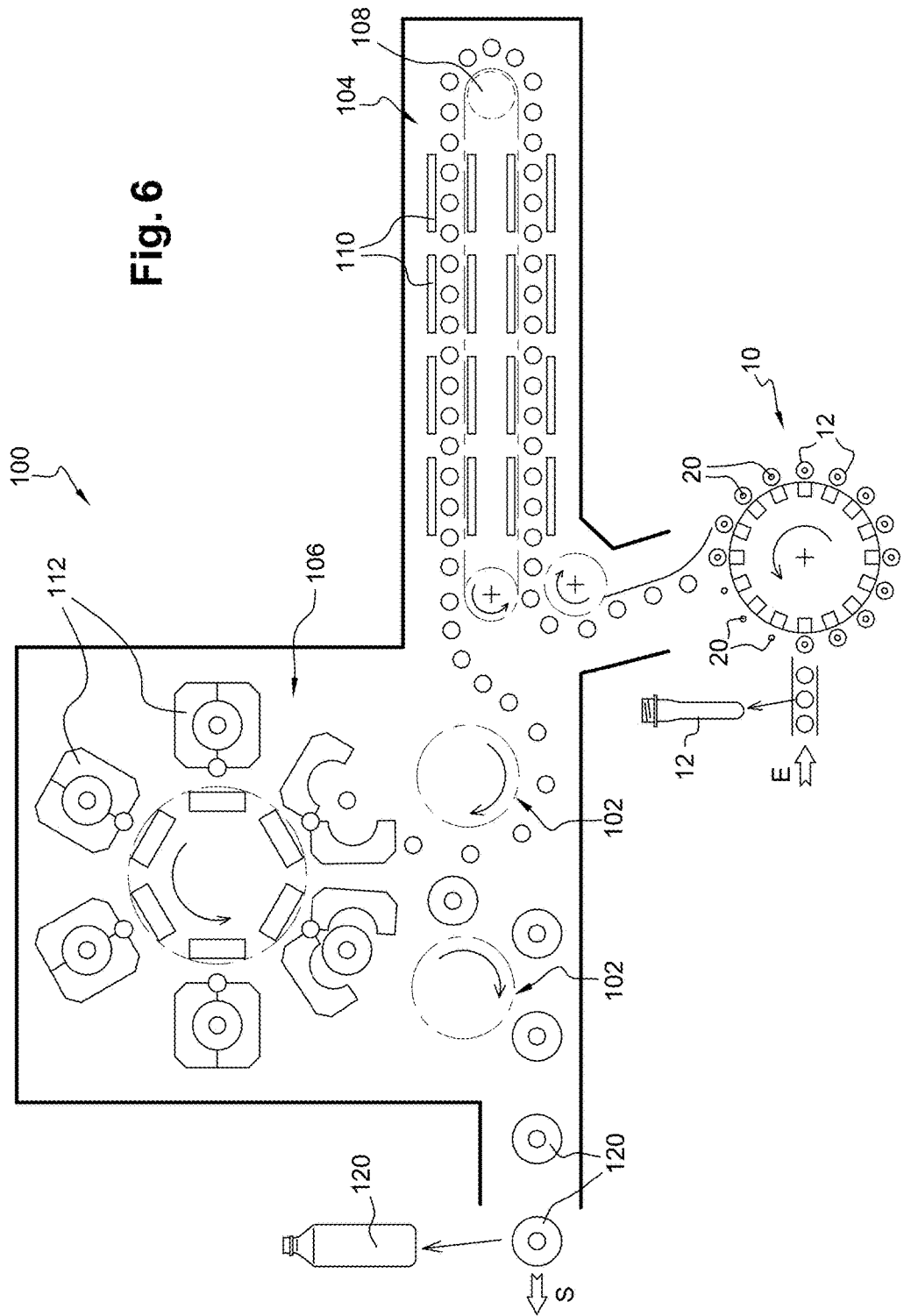
FIG. 6 is a schematic view which shows an installation for the production of a sterile recipient starting from a preform decontaminated by a decontamination device.

FIG. 6 shows one example of an installation 100 for production of sterile recipients, said installation 100 comprising an input E and an output S between which transfer means 102 are disposed that are capable of ensuring, from upstream to downstream, the circulation of a flow of preforms 12 through the recipient production installation 120.

The transfer means 102 comprise for example wheels which are equipped with means for transporting the preforms 12 such as notches or clips.

The installation 100 comprises at least one oven 104 for the heat treatment of the preforms 12, a molding machine 106 (generally called "blower") in which the preforms are transformed into recipients.

Preferably, the installation 100 comprises, downstream of the molding machine 106, a machine (not shown) for filling and for capping sterile recipients 120 exiting from said molding unit 106 and which are transferred by means 102 arranged at the output S.

Advantageously, such an installation 100 comprises at least one device 10 for decontamination by irradiation in order to decontaminate at least the interior of a preform 12.

Preferably and such as shown in FIG. 6, the decontamination device 10 is arranged upstream of the oven 104 for heat treatment of the preforms.

The arrangement of the decontamination device 10 upstream of the oven 104 only however constitutes one non-limiting example of configuration of the device 10 in an installation 100.

Indeed, the decontamination device 10 may be incorporated in various ways into the installation 100 for production of sterile recipients in order to decontaminate a flow of preforms 12 designed to be transformed within it.

As a variant, the decontamination device 10 is integrated into the device 108 for transport from the oven 104 or arranged downstream of the oven 104, notably between the oven 104 and the blowing machine 106, or else integrated into the blowing machine 106.

According to a first example, the support mechanism 20 for the components consists of a shaft of a cleaning system (not shown) inside of a preform 12 which is arranged upstream of the oven 104.

For further details on such a cleaning system, also sometimes called dust-removal system, reference should be made for example to the document WO-99/03513.

Advantageously, the shaft then has a double function, on the one hand, that of cleaning, and on the other, that of decontamination.

In addition, the shaft of the cleaning system is generally hollow in order to allow a flow of air used for performing the dust removal, the air flowing through it then advantageously being able to form a fluid for cooling the components.

According to this first example, the decontamination device 10 therefore provides the functions of dust removal and of decontamination of the preforms 12 designed to be transformed into sterile recipients 120 by virtue of the installation 100.

According to a second example not shown, the movement of the support mechanism 20 for the decontamination means 22 is linked to the means for gripping the preform 12 that a preform transport device 108 equipping the heat treatment oven 104 comprises.

Many examples of gripping means for preforms, otherwise referred to as "mandrills" or "trammels", are known from the prior art, and reference may be made for example to the document WO-00/48819.

The movement of the gripping means for the preforms 12 is linked to a transport device 108 associated with the oven 104 in such a manner as to carry out, in a closed loop, the heating cycle during which the preforms 12 are conditioned thermally by heating means 110 forming a source of infrared radiation, such as lamps.

Preferably, the support mechanism 20 for the components is assembled so as to be mobile in such a manner as to be able to be temporarily retracted during operations for grasping and for releasing the preform 12 on and from the gripping means so as not to interfere with the process.

The support mechanism 20 is advantageously controlled to slide through the gripping means, once the preform 12 has been grasped, so as to introduce the semiconductor components inside of the internal volume 16 of the preform 12.

Advantageously, the decontamination treatment by irradiation of the internal surface of the wall of the preform 12 is then carried out simultaneously with the heat treatment, by virtue of which the decontamination is operated in dead time.

As a result, such a decontamination of the interior of the preforms 12 operated within the oven 104 does not modify at all, with respect to a conventional method, the duration of production of a recipient starting from a preform and moreover allows a long period of irradiation without the production flow being at all impacted.

According to a third example, the decontamination device 10 is integrated into means 102 for transferring the preforms such as those arranged for example between the exit of the oven 104 and the blowing machine 106.

Advantageously, the decontamination is then again performed in dead time and the aforementioned advantages remain.

One exemplary embodiment of a decontamination device 10 is shown schematically in FIG. 6.

The decontamination device 10 is arranged upstream of the oven 104 but could be arranged elsewhere in the installation 100 as has just been described.

The oven 104 is thus fed by a flow of decontaminated preforms 12 coming from said decontamination device 10.

Preferably, the decontamination device 10 has only one function for the decontamination of the interior of the preforms 12.

Preferably, the decontamination device 10 is of the rotatable type and at least the preforms 12 are driven in rotation about a central axis of the device 10.

Advantageously, the device 10 comprises several decontamination stations disposed around the circumference adjacent to one another and each comprising a support mechanism 20 equipped with means 22 for decontamination by irradiation.

The support mechanism 20 is for example a mobile shaft having the role of carrying the decontamination means 22.

The device 10 is supplied with a continuous flow of preforms 12, each preform 12 being transported along a path via means of said device 10 which are for example analogous to known means, such as a notched wheel or a clip.

Advantageously, the support mechanisms 20 are then also assembled so as to be mobile in rotation about the central axis of the device 10 and synchronized so as to follow a preform 12 along the said given path during which the decontamination cycle by irradiation is carried out.

In the case of a device 10 of the rotatable type, the path followed is for example a portion of a circle extending between an entry point where the preforms 12 are admitted into the device 10 and an exit where the preforms 12 leave the device 10 in order to continue their journey in the direction of the oven 104.

As a variant, the stations of the decontamination device 10 are aligned in a rectilinear manner one after the other.

Preferably, the decontamination cycle implemented with the device 10 is carried out on preforms 12 which are moving so that the decontamination does not affect the production flow of the recipients starting from the preforms 12.

As a variant, the decontamination device 10 comprises fixed stations, each preform 12 remaining temporarily immobile for the duration of the decontamination cycle by irradiation.

Advantageously, such a device 10 is arranged upstream of the oven 104 and the decontamination performed on the flow of preforms 12 feeding the oven.

Preferably, at least one buffer area is then created so as to be able to decontaminate a batch comprising a given number of preforms 12 but nevertheless without interrupting the flow of preforms 12 feeding the oven 104.

Advantageously, a batch of preforms 12 is extracted from the flow in order to be decontaminated in the device 10 then is reintegrated into the former. Preforms 12 are thus successively admitted, treated according to the decontamination cycle previously described and evacuated downstream in order to allow the admission of a new batch of preforms.

Preferably, the decontamination means 22 of the device 10 comprise components of the semiconductor type such as the diodes 22C and 22A respectively capable of emitting ultraviolet radiation of the UVC and UVA type and forming a first and a second group of components.

Preferably, the means 110 for heating by infrared equipping the oven 104 then form the components of the third group (as a variant the second group) emitting infrared radiation which is combined with UVC and/or UVA ultraviolet radiation.

Indeed and in contrast to the ultraviolet radiation, the infrared radiation is capable of passing through the wall 14 of the preform 12 made of a thermoplastic material such as PET.

The infrared radiation is therefore capable of being applied from the outside of the preform 12 in order to decontaminate its interior.

As a variant, the components of the third group (as a to variant the second group) emitting infrared radiation are carried by the support mechanism 20 and are therefore also introduced into the interior of the preform 12.

According to a fourth example illustrated in FIG. 7, the support mechanism 20 for the components consists of a shaft which is associated with a molding unit 112 of a molding machine 106 of the installation 100.

Preferably, such a shaft is permanently mounted on the molding unit 112 notably in order to avoid all assembly/disassembly operations by an operator.

Advantageously, the molding unit 112 comprises associated actuation means able to be selectively controlled for retracting the support mechanism 20 from a position of use toward a standby position and vice versa.

Advantageously, the support mechanism 20 for the components consists of a shaft for drawing from the molding unit 112.

As is shown in FIG. 7, the molding unit 112 comprises at least two half-molds 50 which are assembled so as to be mobile with respect to one another between at least an open position and a closed position of the unit.

Here, the molding unit 112 is of the "coffin" type, in other words at least one of the half-molds 50 is assembled so as to be mobile in rotation about an axis A with a vertical orientation.

In the closed position, the half-molds of the molding unit 112 are brought together in a joining plane with a vertical orientation.

Each half-mold 50 is equipped with a molding imprint, the uniting of the imprints in the closed position of the molding unit 112 determining a molding cavity.

As a variant not shown, the molding unit 112 comprises a separate mold base, complementary to the half-molds 50.

Such a molding unit 112 is designed for the fabrication of a recipient. The final recipient is obtained starting from a preform 12 which, having been previously heat treated in an oven 104, is for example transformed by blowing or by drawing-blowing in the molding unit 112.

The molding unit 112 generally constitutes one of the is stations of a blowing machine 106 or "blower" of an installation 100 for the production of recipients. A blowing machine 106 with a "rotational" design comprises a plurality of molding units 112 distributed around a circumference.

During the fabrication of the recipient, the preform 12 extends through the opening 114 of the molding unit 112, the body 40 inside of the molding cavity and the neck 44 having its definitive shape remaining on the outside.

The wall of the unit 112 comprising the molding imprint is designed to be in contact with the external surface of the body of the sterile recipient 120 resulting from the transformation of the decontaminated preform 12.

In the various examples described beforehand, the support mechanism 20 for the decontamination means 22 of the device 10 is preferably a shaft which is assembled so as to be mobile in such a manner as to be temporarily introduced into the interior of the preform 12 then extracted and which has a fixed length (or height) and a constant diameter.

As a variant, the support mechanism 20 has an external diameter which decreases along the axis X in the direction of its free end.

Such a variation of the diameter of the support mechanism 20 advantageously allows it to be introduced as far as the bottom 42 of the preform 12 even when the space is narrow.

As a variant not shown, the support mechanism 20 has a variable length. Advantageously, the support mechanism 20 is a telescopic shaft formed from an assembly of mobile sections able to be retracted by sliding into one another.

Advantageously, such a support mechanism 20 of the telescopic type then has an external diameter that decreases along the axis X in the direction of its free end The invention furthermore provides a method for fabricating a sterile recipient 120 starting from a preform 12 made of thermoplastic material, said method comprising at least one initial step consisting in fabricating a preform 12 made of thermoplastic material and a final step consisting in transforming said preform 12 into a recipient 120 and being characterized by the fact that, between said initial and final steps, said method comprises at least one intermediate step for decontaminating at least the interior of the preform 12 consisting at least in:
 introducing into the interior of the preform 12 means 22 for decontamination by irradiation formed by components of the semiconductor type capable of selectively emitting at least one type of ultraviolet radiation;
 controlling said components of the semiconductor type so as to cause the emission of at least one type of ultraviolet radiation in order to irradiate the interior of the preform 12;
 extracting said decontamination means 22 outside of the decontaminated preform 12.

The decontamination of the interior of the preforms 12 with a decontamination device 10 is implemented prior to the fabrication of the recipients in order to directly obtain sterile recipients 120.

Advantageously, the sterile recipients 120 obtained starting from the decontaminated preforms are indeed able to be directly filled and closed, for example by capping, within the installation 100.

The invention claimed is:
1. An assembly comprising:
   at least one preform made of thermoplastic material for the fabrication of a recipient, the preform comprising a neck which is axially extended by a body closed by a bottom and which bounds an opening for access to the interior of said preform; and
   a decontamination device configured to decontaminate the interior of the preform, the decontamination device comprising
   at least one support mechanism positioned into the interior of the preform and carrying a plurality of semiconductor components configured to decontaminate by irradiation and configured to be introduced via the opening into the interior of said preform in order to selectively emit at least one type of ultraviolet radiation inside of the preform to be decontaminated.
2. The assembly as claimed in claim 1, wherein at least one of the components forming said irradiation device emits ultraviolet radiation of the "C" type exhibiting at least one main emission line having a wavelength in the range between 100 nm and 280 nm.

3. The assembly as claimed in claim 1, wherein at least one of the components forming the irradiation device emits ultraviolet radiation of the "A" type exhibiting at least one main emission line having a wavelength in the range between 315 nm and 400 nm.

4. The assembly as claimed in claim 1, wherein the irradiation device comprises the components forming at least a first group of one or more components and a second group of one or more components, at least the first group of components comprising at least one component which emits ultraviolet radiation exhibiting at least one main emission line having a wavelength in the range between 100 nm and 400 nm.

5. The assembly as claimed in claim 4, wherein the second group of components comprises at least one component which emits infrared radiation having at least one main emission line having a wavelength in the range between 780 nm and 1 mm.

6. The assembly as claimed in claim 1, wherein said decontamination device comprises an actuator selectively controlled to cause a relative movement between the support mechanism and the preform in order to temporarily introduce the irradiation device into the interior of the preform.

7. The assembly as claimed in claim 1, wherein the irradiation device comprises the components which are arranged on all or part of the height of the section of the support mechanism configured to be received inside of the preform.

8. The assembly as claimed in claim 1, wherein the irradiation device comprises the components which are arranged around the whole of the periphery of the support mechanism in order to emit radiation in all directions, over substantially 360°, to decontaminate the interior of the preform.

9. The assembly as claimed in claim 1, wherein the support mechanism for the components is driven selectively in rotation to scan the interior of the preform with at least one type of ultraviolet radiation.

10. The assembly as claimed in claim 1, wherein the decontamination device comprises a control unit selectively controlling the components in order to regulate the emission or otherwise of said at least one type of ultraviolet radiation.

11. The assembly as claimed in claim 1, wherein the support mechanism for the components comprises a shaft configured to draw from a preform molding unit for the fabrication of recipients.

12. The assembly as claimed in claim 1, wherein the decontamination device comprises a cooling system configured to cool the components, said cooling system being composed at least of the support mechanism evacuating at least by conduction the heat produced in operation by said components.

13. The assembly as claimed in claim 12, wherein the support mechanism comprises a cooling circuit configured to selectively establish a circulation of a cooling fluid inside of the support mechanism.

14. The assembly as claimed in claim 1, wherein at least a part of the components forming the irradiation device are light-emitting diodes.

15. The assembly as claimed in claim 1, wherein at least a part of the components forming the irradiation device are laser diodes.

16. An installation for producing sterile recipients starting from preforms each made of thermoplastic material comprising a neck which is axially extended by a body closed by a bottom and which bounds an opening for access to the interior of said preform, said installation comprising:
   an oven for heat treatment of the preforms;
   a blowing machine configured to transform, at least by injection of a fluid under pressure, said preforms into recipients; and
   at least one decontamination device configured to be positioned into the interior of the preform for the decontamination of the preforms comprising
      at least one support mechanism carrying a plurality of semiconductor components configured to decontaminate by irradiation and configured to be introduced via the opening into the interior of said preform in order to selectively emit at least one type of ultraviolet radiation inside of the preform to be decontaminated.

17. The installation as claimed in claim 16, wherein said decontamination device is disposed upstream, in or downstream of the heat treatment oven.

18. A method for fabricating a sterile recipient starting from a preform made of thermoplastic material, said method comprising:
   fabricating a preform made of thermoplastic material;
   decontaminating at least the interior of the preform by
      positioning into the interior of the preform at least one support mechanism carrying a plurality of semiconductor components configured to decontaminate by irradiation and configured to selectively emit at least one type of ultraviolet radiation,
      controlling said semiconductor components to cause the emission of at least one type of ultraviolet radiation in order to irradiate the interior of the preform, and
      extracting said irradiation device outside of the decontaminated preform; and
   transforming said preform into a recipient.

19. The method as claimed in claim 18, further comprising heat treating the preform before transforming the preform into the recipient.

20. The method as claimed in claim 19, wherein the transforming the preform into the recipient comprises injecting a fluid under pressure into the interior of the previously heat-treated preform that is disposed in a molding unit configured to mold the recipient.

21. The assembly as claimed in claim 1, wherein the diameter of the neck is in a range between 20-35 mm.

22. The assembly as claimed in claim 1, wherein the support mechanism carrying the semiconductor components is positioned in the interior of the preform without any contact with the preform.

* * * * *